United States Patent [19]
Csongor

[11] Patent Number: 5,939,015
[45] Date of Patent: *Aug. 17, 1999

[54] CENTERCORE PROCESS FOR GAS ASSISTED INJECTION MOLDING

[76] Inventor: Desider G. Csongor, 19 Bennett St., Manchester, Mass. 01944

[*] Notice: This patent is subject to a terminal disclaimer.

[21] Appl. No.: 08/816,669

[22] Filed: Mar. 13, 1997

Related U.S. Application Data

[60] Division of application No. 08/511,055, Aug. 3, 1995, Pat. No. 5,670,112, which is a continuation-in-part of application No. 08/393,200, Feb. 23, 1995, abandoned.

[51] Int. Cl.⁶ .......................... B29C 45/18; B29C 45/50
[52] U.S. Cl. ................................ 264/572; 425/130
[58] Field of Search ...................... 264/45.1, 50, 572, 264/241, 255; 425/130, 131.1, 133.1, 523, 532, 380, 381, 382 R, 207, 382.4

[56] References Cited

U.S. PATENT DOCUMENTS

| | | | |
|---|---|---|---|
| 3,163,693 | 12/1964 | Stenger | 425/532 |
| 3,387,331 | 6/1968 | Billings | 425/381 |
| 3,694,424 | 9/1972 | Hunkar et al. | 264/526 |
| 3,890,416 | 6/1975 | Bauer et al. | 264/45.5 |
| 4,770,624 | 9/1988 | Ziegler | 425/382.4 |
| 4,859,068 | 8/1989 | Sironi | 425/130 |
| 5,670,112 | 9/1997 | Csongor et al. | 264/572 |

FOREIGN PATENT DOCUMENTS 1590381  6/1981  United Kingdom ............... 264/171.2

*Primary Examiner*—Catherine Timm
*Attorney, Agent, or Firm*—Don Halgren

[57] ABSTRACT

The present invention comprises a method for delivering a medium such as a gas, vapor or liquid into a melted plastic in a mold via an elongated screw shaft rotatably supported in a housing, the method including the steps of providing the screw shaft with a bore longitudinally therethrough from a proximal end to a distal tip end thereof, rotating the screw shaft in the housing to move plastic therethrough, and into the mold, introducing a gas, vapor or liquid into the bore, to permit the gas, vapor or liquid to be delivered through the bore, and into the molten plastic in the mold through the distal tip end of the screw shaft.

9 Claims, 7 Drawing Sheets

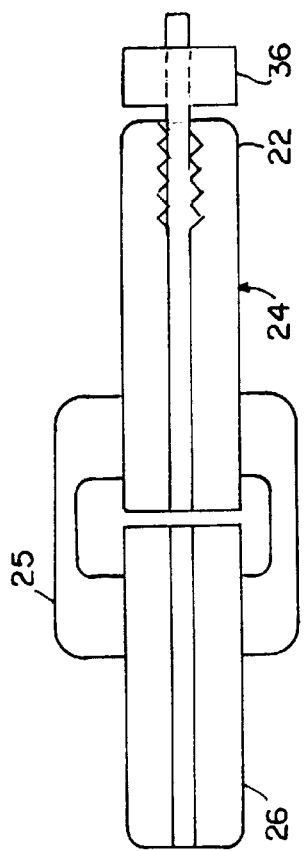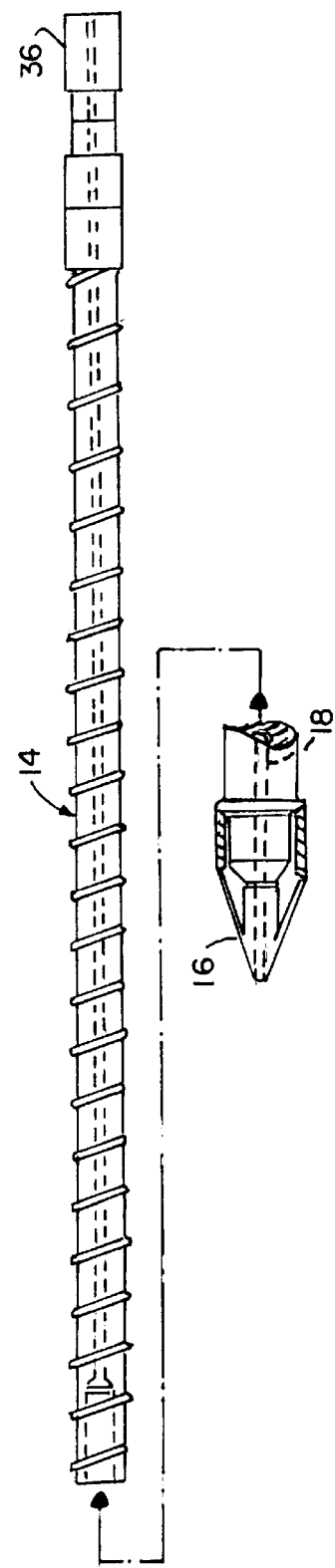

CENTERCORE PROCESS FOR GAS ASSISTED INJECTION MOLDING

This Application is a Divisional Application of our earlier filed U.S. patent application Ser. No. 08/511,055, filed Aug. 3, 1995, now U.S. Pat. No. 5,670,112 which is incorporated herein by reference in its entirety, which is a Continuation-in-Part of our earlier filed application Ser. No. 08/393,200 filed Feb. 23, 1995, now abandoned, which is incorporated herein by reference in its entirety.

BACKGROUND OF THE INVENTION

1. Field of the Invention

This invention relates to the simultaneous or sequential introduction of multiphase matter into a plastic melt through a plasticating screw.

2. Prior Art

Heretofore, plastic in molds or dies have been treated by introduction of matter through the wall of the mold, for cooling or the like, or matter has been added only to the plastic as it is worked between the plasticating screw and the housing in which it is rotatively supported.

BRIEF SUMMARY OF THE INVENTION

The present invention discloses a novel way to introduce high pressure gas, vapors and/or liquids into the process of manufacturing plastic material by a plasticating screw machine. The invention comprises drilling (coring) a hole axially through a plasticating screw of appropriate size to accommodate the introduction of gas, vapors and/or liquids into the melt shot.

A non return shut off valve may be arranged on the tip of that plasticating screw, which valve is made with a drilled hole through it including the tip so that during or after the injection phase (short shot) or in the process of completion the tip opens either due to air pressure, mechanical actuation (spring loaded) etc. to allow the assist gas, vapors or liquids to hollow out the plastic part, where that screw is utilized in an injection molding operation. A finely controlled gas (typically nitrogen) pressure and volume may be applied to the driving (proximal) end of the plasticating screw by means of a rotational collar. The gas will pass through the length of the screw to the non return shut off valve, or tip, where it will enter the molten plastic material. Required gas volume or material viscosity may necessitate fine gas entry apertures such as with a jewelled orifice and/or a gas check valve to prevent material from blocking gas passages. A typical processing sequence will be incorporated to the gas cycle. The part will be a short shot. The screw will remain fully forward through the second stage while gas is applied (no cushion). After this phase, allowances must be made for venting or degassing of the unnecessary gas before the part is ejected, when utilized in an injection molding format. The introduction of gas, vapors, or liquids into the plasticating screw is from the rear of the screw in one embodiment, or from a design mated entry point, such as a radial channel from a collar radially outwardly of the screw and into the core of the reciprocating injection screw in a further embodiment. Assist media is proportionally regulated via the described gas control system to allow for maximum efficiency of profiling.

A description of the mechanical aspects of the invention includes: (a) Injection screw coring for the introduction of gas, vapor, or liquids (fluids); (b) Non return shut off valve threaded onto the delivery end of the plasaticating screw for the purpose of: (1) shuting off the backflow of the molten plastic during an injection, holding and cooling phase of the plastic, (2) Enhancing the mixing of the molten plastic, (3) Allowing for the passage of high pressure gas, vapors or liquids through the center hole drilled (to specific size) through the center of the injection screw tip (aka non return valve), (4) Prevent plastic coming into center core during the screw recovery or plastification phase.

The center bore in the plasatication screw is arranged to accommodate the passage of gas, vapor, liquids through the screw injection tip under certain pressures and temperatures. The center core hole should also be able to accommodate single, double or multiphase coaxial tubes for the passage of multiphase materials with a conveying point in the injection tip. Temperature control is of paramount value for the constituent plastics being worked.

A high pressure rotary union may be arranged at the back end of the screw depending as to whether constituents are introduced axially or radially.

The phase process for injection molding plastics utilizing the center cored screw comprises: (a) Injection phase: control by a control circuit of the melt and high pressure gas, vapor, or liquid and temperature control thereof, (b) Holding and Cooling phase: control of gas, vapor, or liquid pressure and temperature for efficient cooling of the molded parts to control surface finish and part shrinkage. This is accomplished by: (1.) Introduction of gas, vapor, or liquid simultaneously (without a time delay) using control circuit components comprising a further embodiment of the present invention; or (2.) Introduction of gas, vapor, or liquid sequentially (after a preprogrammed time delay) the control circuit components of the present invention; (3.) Temperature control of the gas to provide an optimal "gas bubble", coring, or tunneling, or thereof into the plastic melt; and (4.) Profiling of gas pressure by use of software with a programmed capability to ramp or step up the gas pressure using a menu driven system allowing various time/pressure durations in the gas injection phase.

A PID (proportional integral derivative) controlled microcontroller, comprises a further embodiment of this invention. This Proportional Controller is a closed loop PID controlled pressure regulating system, having a digital (LCD) display used as an attachment to commercially available gas control systems.

The proportional control is achieved through an electro-pneumatic circuit with a proportional regulator (or valve) pilot operating a booster unit which then pilot operates a high pressure regulator. Low pressure compressed air 0.55–0.70 MPa (typically 80–150 psi) is used as a control pressure which then regulates the pressurized gas to desired levels up to a maximum of 103 MPa (~15,000 psi max.). With this system, as the low pressure signal is boosted to the respective high pressure setting, it "loads" a "dome loaded" high pressure regulator. The proportional regulation is controlled by a Pulse Width Modulating (PWM) controller operating a normally closed on/off three way valve . Upon the completion of the cycle, the line pressure from the gas tubing can be vented through a vent port in the "dome" regulator.

A downstream high pressure transducer attached to the gas line provides feedback to the micro-controller thus adjusting the PWM proportional valve to the set point (closed loop). This closed loop system with a full PID control algorithm and controlled by the micro-controller allows the gas pressure to be controlled via a voltage (or current) profile thus creating an infinite number of pressure versus time settings. An on-board RS232 interface allows the capability to capture the information from the gas pressure transducer before the gas enters the mold and thus may be used as a monitoring and statistical tool. A PC displays a menu system, where pressure can be profiled either up or down as a geometric function.

A digital display is arranged to show the pressure set point and the actual value (during cycle). The micro-controller (PWM) is driven using a separate 0–24 VDC, 4.0 amps max. rated regulated power supply. Ports for the pressure sensor, RS232, allow for data acquisition and valve control signals (#1, #3, #5, #6) allow voltage input into the controller board. Using the up/down keys, the pressure settings are easily adjusted within a pressure sensitivity scale of ±1 psi and can be seen on screen as setpoint vs. actual. Adjustments to the software are made using diagnostics modeand coarse adjust. The response time of the PID controller from the start of the cycle to reaching the setpoint is approximately 50 milliseconds (response time can be adjusted to specific needs).

A prototype of the micro-controller is currently used with the gas control system on for example, a 250 Ton 32 oz. Cincinnati Milacron injection molding machine as an added feature to study the process parameters of the gas-assisted injection molding process.

A Gas-Assist Controller system will be attached to an existing commercial gas unit utilizing the volume controll technique and will be operational as an integrated attachment. The system has features for multiple independent channels (if needed), closed loop control, 0–5 VDC control signals, PID control algorithm, pulse width modulating (PWM) outputs, option for extra pressure transducers, input signal conditioning, RS232 monitor, and operator interface (Keyboard/LCD).

Equipment operation for gas heating/cooling by this system would allow for pressurization of $N_2$ by the gas ($N_2$) itself or shop air (150 psi), whichever suits per need.

If $N_2$ is not used as a control mechanism, a Tee fitting and gas regulator would be eliminated from the overall system operation. A high pressure gas (up to 15,000 psi) may be used as both the control mechanism as well as the actual set pressure gas to hollow out the molten plastic. A proportional regulator is arranged to provide precise pressure control with a flow control valve loading a "Dome" loaded high pressure regulator to make the gas setpoint (set on the PID controller). A second Tee fitting may be used as a split for the gas injection stage and the gas packing/holding/cooling state.

During the gas injection stage, once the gas has reached the setpoint at the "dome" regulator, a first circuit would allow the actuation of a 2 way solenoid valve. At this point, a heat exchanger heating element of the system would heat the gas to a desired set temperature and fill the gas into the accumulator. At this point, both the pressure and the temperature would be measured by a pressure transducer and a temperature sensor. Next, a solenoid valve is arranged in the system to open and allow the free passage of pressurized gas through a fixed jewel orifice and into the mold cavity. A pressure sensor and a temperature sensor may be placed before the jeweled orifice to measure the pressure and temperature just before the gas enter the mold.

Upon the completion of gas injection cycle, the solenoid valves are arranged to close. The $N_2$ would now be diverted to a second circuit where a humidifier device may add small amounts of $H_2O$ to the $N_2$ and the components would be cooled to a set temperature by a heat exchanger cooling element in the system. Again, a 2 way solenoid valve is arranged to open, allowing the mixture to pass through the orifice with pressure sensor and temperature sensor recording the pressure and temperature of the cold mixture. This phase of the cycle would assist in making hollow injected molded parts.

Thus the invention includes: (1) a gas injection molding system comprising a screw for delivering plastic material to a mold and a gas injection jeweled orifice port through the screw tip for injecting gas, vapor, or liquids into the plastic in the mold; (2) a gas injection closed loop pressure control system using a dome regulator ratio device with a microprocessor based control system to profile (ramp/step) the gas injection using a menu driven system allowing various time/pressure durations in the gas injection phase and the gas holding/packing phase. This can be either a personal computer (PC), Programmable Logic controller (PLC) or an embedded system with either a Proportional Integral Derivative (PID) or FUZZY logic algorithm; and (3) a control system for controlling the temperature of the gas during the injection phase and cooling phase.

The invention further includes a control for the injection stage velocity of the gas. A controlled pressure in a tank is arranged to deliver a controlled velocity through a fixed jeweled orifice. Due to the sonic flow of gas [If, $P1+1.013<=1.896 (P2+1.013)$ then the flow rate is dependent only on the orifice size and supply pressure, P1].

The temperature of the gas may be heated by a heater. This will increase the gas viscosity thus limiting or helping prevent "gas blow out" from the molded part during the process cycle. It will also add to the temperature uniformity which will decrease the tendency of the part to have sink marks due to the thermal differences between the melt, mold and gas.

Once the mold has been filled and the part has been properly cored out with gas, pressure control is necessary to keep the part "packed" and reduce the sink effect. This will be accomplished by switching to the second portion (part B) of circuit which regulates pressure only. This will allow for pressure profiling in the holding/packing phase depending upon the part geometry and material. Simultaneously we will be introducing water ($H_2O$) to the nitrogen ($N_2$) mixture. This will enter the hollow core of the part thus providing a faster cooling phase, leading to a decrease in cycle time. The after cooler may not be necessary as the effect of phase change of liquid to steam of the $H_2O$ may remove sufficient heat.

It is proposed to inject other gases into the plastic hollow part once it has expanded. A number of gases can be used. One such effective way is to have a phase change in the part for doing the cooling. A mixture of cold air with water spray will convert the spray into ice crystals which are conveyed with the air and once they hit the inside of the plastic part the ice will convert the water vapor with a large latent heat of sublimation (about 1100 Btu/lb). As the ice sublimates, the pressure will increase and a control device will allow the part to be vented via a pressure regulator after which the process of air/ice injection is repeated until the part is sufficiently cooled.

Alternatively one can inject liquid $CO_2$ (>=80 psi). The liquid turns to dry ice at P<=80 psi and then vaporizes (sublimates) when it contacts the internal wall of the part. A third method would be to use liquid nitrogen. The liquid would evaporate and extract heat from the inside of the part. Also, the nitrogen ($N_2$) could be recovered.

In the present invention. The hydraulic injection cylinder is coupled to the screw shank for inject and retract functions.

The screw shank may also pass through a gearbox which provides rotation during plasticizing. The flight includes feed, transition, and metering sections of the screw. The screw tip or valve will typically incorporate a check ring or ball.

BRIEF DESCRIPTION OF THE DRAWINGS

The objects and advantages of the present invention will become more apparent when viewed in conjunction with the following drawings, in which:

FIG. 3 is a longitudinal sectional view taken of a plasticating screw showing both radial entry and axial entry embodiments for delivery of gas into the axial center core for introduction into a plastic melt through the screw tip;

FIG. 4 is an exploded view of a plasticating screw with a non-return valve on its distal end;

DESCRIPTION OF THE PREFERRED EMBODIMENTS

Figure 1:
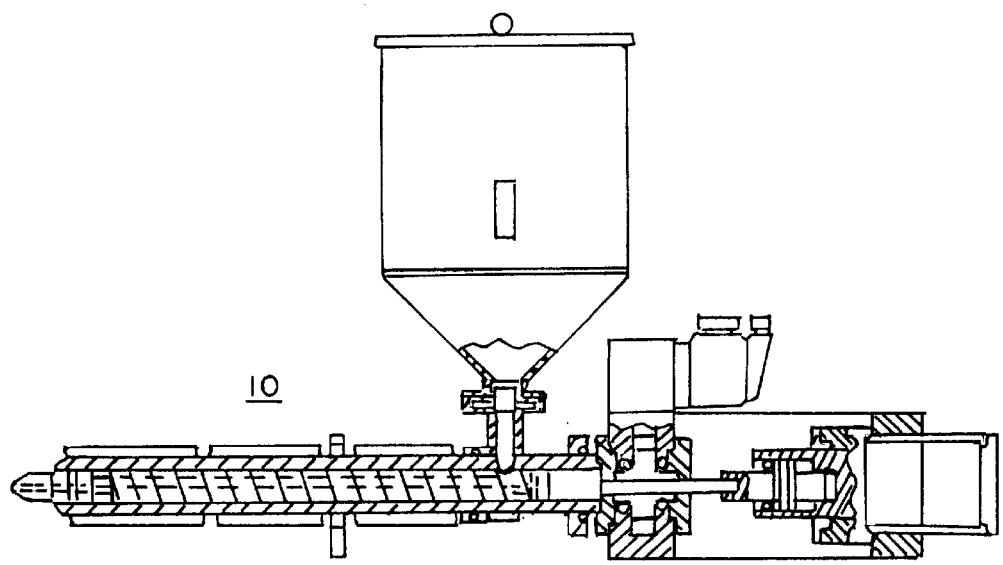
FIG. 1 is a side elevational view of a plasticating machine assembly, partly in section.
Figure 2:
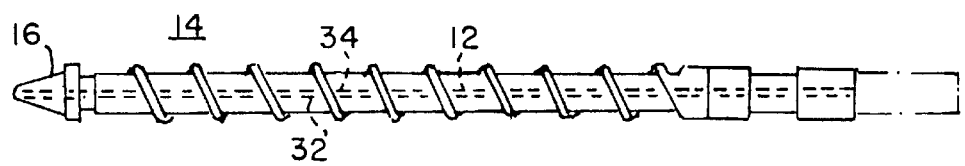
FIG. 2 is a side elevational view of a plasticating screw with a valve shown arranged on its distal tip end.
Figure 5:
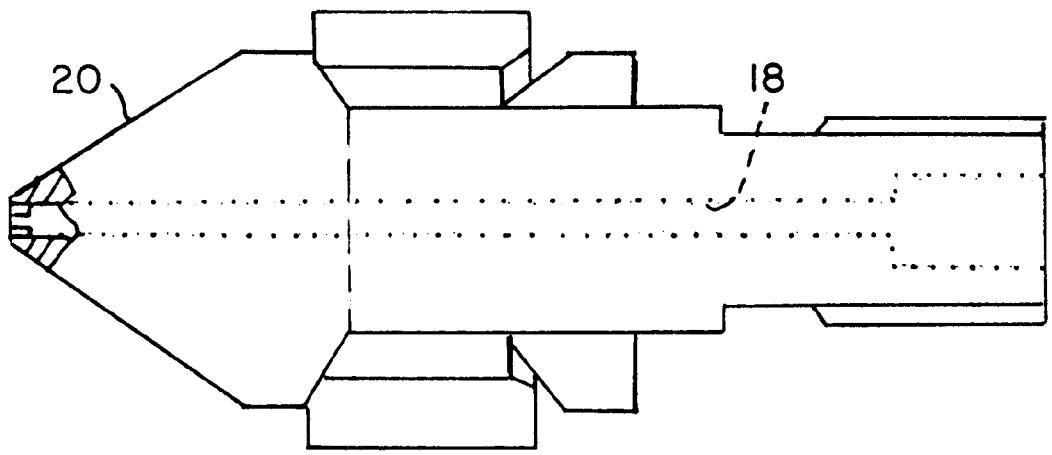
FIG. 5 is a side elevational view of a non-return valve.
Figure 6:
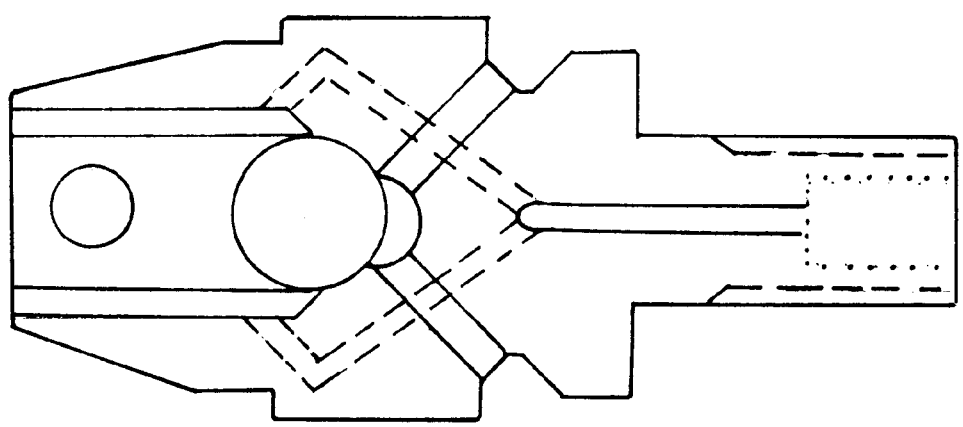
FIG. 6 is a schematic view of a ball check valve.
Figure 7:
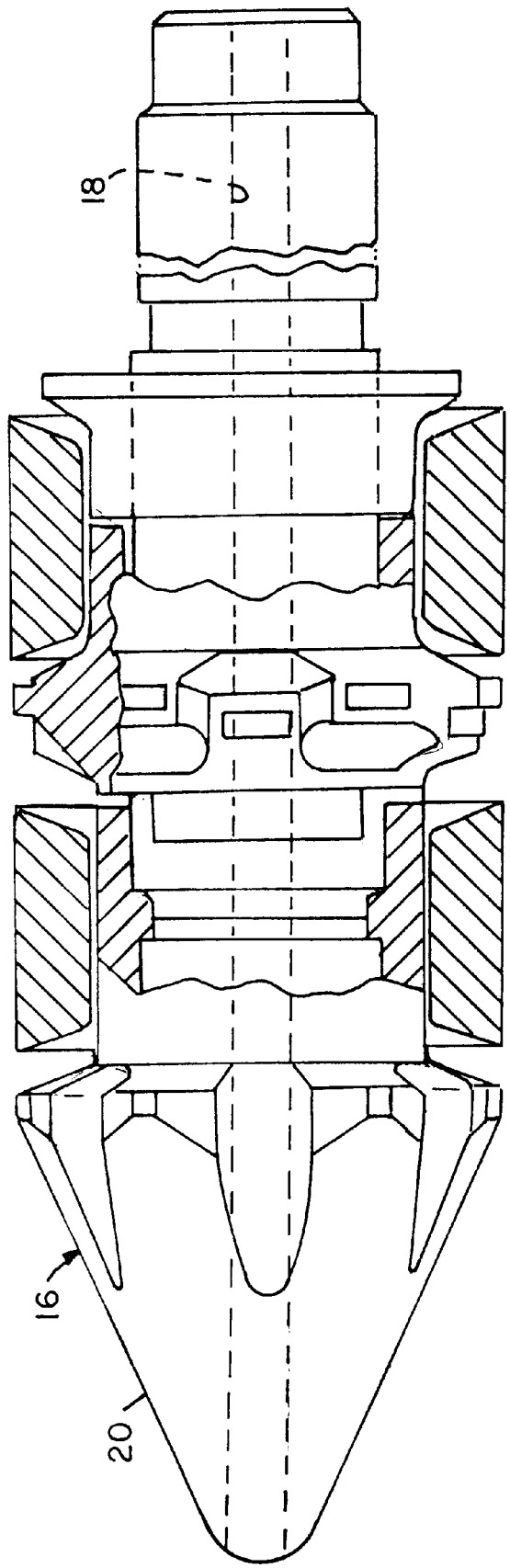
FIG. 7 is a side elevational view of a non-return valve and portions of a screw shaft therewith.

Referring now to the drawings in detail, there is shown a sectional view of a reciprocating screw injection molding machine 10 arranged to introduce high pressure gas, vapors or liquids to assist injection molding of plastic material. This process is based on drilling (coring) a hole 12 axially through a reciprocating plasticating screw 14 as shown in FIG. 2, the hole 12 being of appropriate size to accommodate the introduction of gas, vapors or liquids into the melt shot. Also, a non return shut off valve 16, as may be seen on the distal tip of the screw in FIG. 2, and shown also in FIG. 4, is shown more completely in FIGS. 5, 6 and 7, would be made with a drilled hole 18, through it, including the tip 20, so that during or after the injection phase (short shot) or in the process of completion the tip 20 opens either due to air pressure, mechanical actuation (spring loaded) etc. to allow the assist gas, vapors or liquids to hollow out a plastic part being manufactured. A finely controlled gas (typically nitrogen) pressure and volume may be applied to the driving end 22 of the screw 24 by means of a rotational collar 25, where possible, as may be seen in FIG. 3. The gas will pass through the length of the screw 24 to the non return shut off valve, or tip 26, where it will enter the molten material. Required gas volume or material viscosity may necessitate fine gas entry apertures and/or gas check valving to prevent material from blocking gas passages. A typical processing sequence will be incorporated to the gas cycle. The part will be a short shot. The screw 24 will remain fully forward through the second stage while gas is applied (no cushion). After this phase, allowances must be made for venting or degassing of the unnecessary gas before the part is ejected. The introduction of gas, vapors, or liquids is from the rear (or design mated radial entry point to the core of the reciprocating injection screw, as described hereinbelow), and assist media is proportionally regulated via the described gas control system to allow for maximum efficiency of profiling.

The injection screw hole should accommodate the passage of gas, vapor, liquids through the screw injection tip under certain pressures and temperatures. The center core hole 12, as shown for example in FIG. 2, should also be able to accommodate single, double or multiphase coaxial tubes 32, and 34, for the passage of multiphase materials with a conveying point in the injection tip. Temperature control is of paramount value for the constituent.

A high pressure rotary union 36 is attached at the back (proximal) end of the screw 24, shown in FIGS. 3 and to the back of the screw 14, in FIG. 4, whether constituents are introduced axially or radially.

Figure 8:
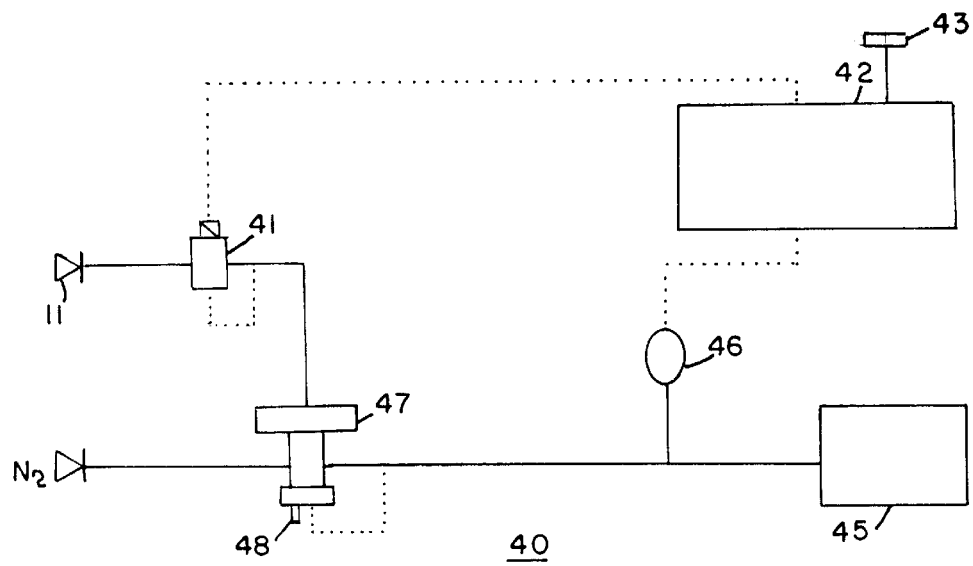
FIG. 8 is a schematic representation of the control circuit for the present invention.

A closed loop PID controlled pressure regulating system 40, is shown in schematic form, in FIG. 8, with a digital (LCD) display may be used as an attachment to a commercially available gas control systems.

The proportional control is achieved through an electro-pneumatic circuit with a proportional regulator (or valve) 41 pilot operating a booster unit through which the pilot operates a high pressure regulator 47. A low pressure compressed air 0.55–0.70 MPa (typically 80–150 psi) source 11, is used to control pressure which then regulates the pressurized gas to desired levels up to a maximum of 103 MPa (~15,000 psi max.). With this system, as the low pressure signal is boosted to the respective high pressure setting, it "loads" the "dome loaded" high pressure regulator 47. The proportional regulation is controlled by a Pulse Width Modulating (PWM) controller 42 operating the normally closed on/off three way valve 41. Upon the completion of the cycle, the line pressure from the gas tubing can be vented through a vent port 48 in the "dome" regulator.

A downstream high pressure transducer 46 attached to the gas line provides feedback to the micro-controller thus adjusting the PWM proportional valve to the set point (closed loop). This closed loop system with a full PID control algorithm and controlled by the micro-controller allows the gas pressure to be controlled via a voltage (or current) profile thus creating an infinite number of pressure versus time settings. An on-board RS232 interface unit 43 allows the capability to capture the information from the gas pressure transducer before the gas enters the mold 45 and thus be used as a monitoring and statistical tool. A PC may display a menu system, where pressure can be profiled either up or down as a geometric function.

Figures 9A, 9B:
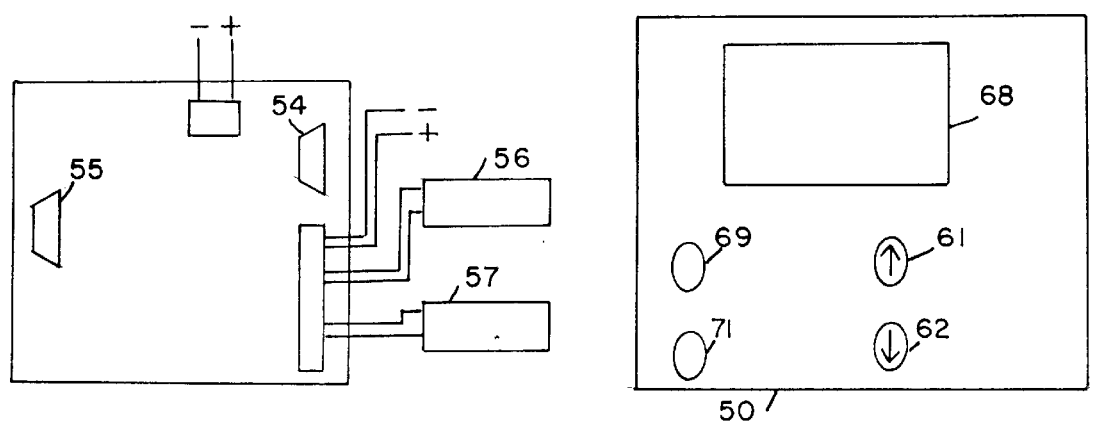
FIGS. 9a and 9b represent schematic and panel layouts of the controller portion of the control circuit of the present invention.

A digital display panel 50 shown in FIG. 9b shows the pressure set point and the actual value (during cycle). The micro-controller (PWM) is driven using a separate 0–24 VDC, 4.0 amps max. rated regulated power supply 57, as shown in FIG. 9a. Ports for the pressure sensor 55, and RS232 54, allow for data acquisition. Valve control signals 56 allow voltage input into the controller board. Using the up/down keys 61 and 62 shown in FIG. 9b, the pressure settings are easily adjusted within a pressure sensitivity scale of ±1 psi and can be seen on screen 68 as setpoint vs. actual. Adjustments to the software are made using diagnostics mode switch 69 and coarse adjust switch 71. The response time of the PID controller from the start of the cycle to reaching the setpoint is approximately 50 milliseconds (response time can be adjusted to specific needs).

Figure 10:
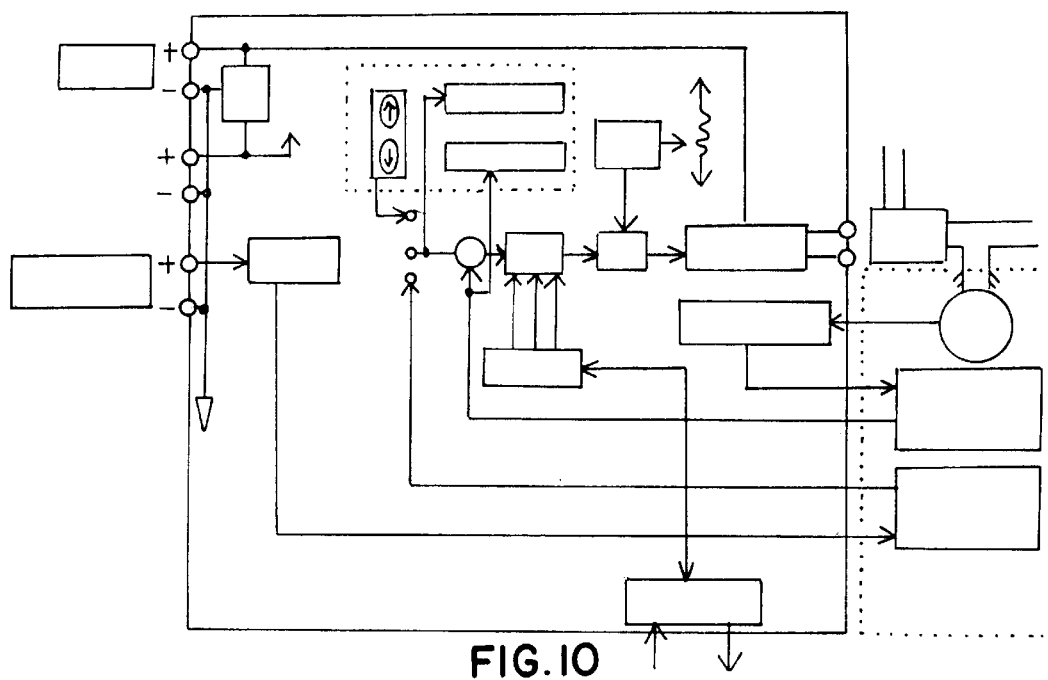
FIG. 10 is a block diagram for one channel of the controller of the present invention.

The logic diagram of the micro-controller is shown in FIG. 10. A prototype of the micro-controller is currently used with the gas control system for example, on a 250 Ton 32 oz. Cincinnati Milacron injection molding machine as an added feature to study the process parameters of the gas-assisted injection molding process.

Figure 11:
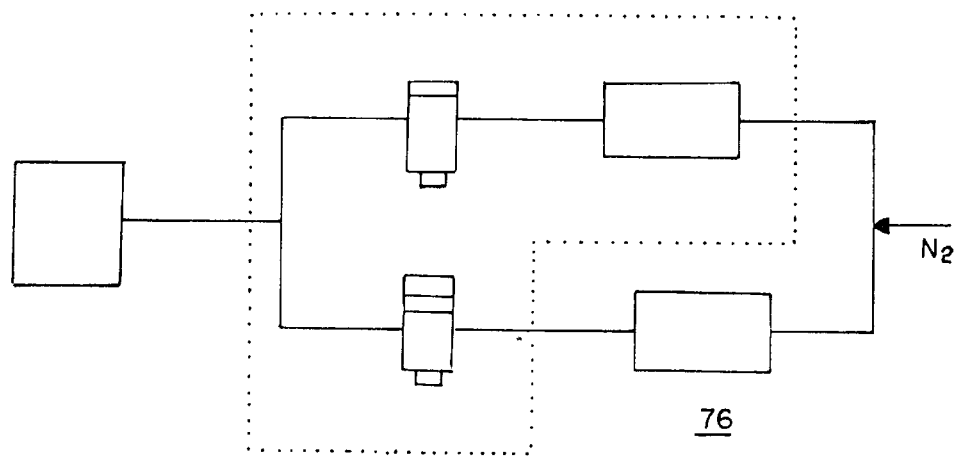
FIG. 11 is a schematic diagram of gas supply components for the present invention.

FIG. 11 is a schematic diagram of a gas supply system 76 for the present invention. The system 76 may be attached to an existing commercial gas unit utilizing the volume controlled technique and may be operational as an integrated attachment.

Figure 12:
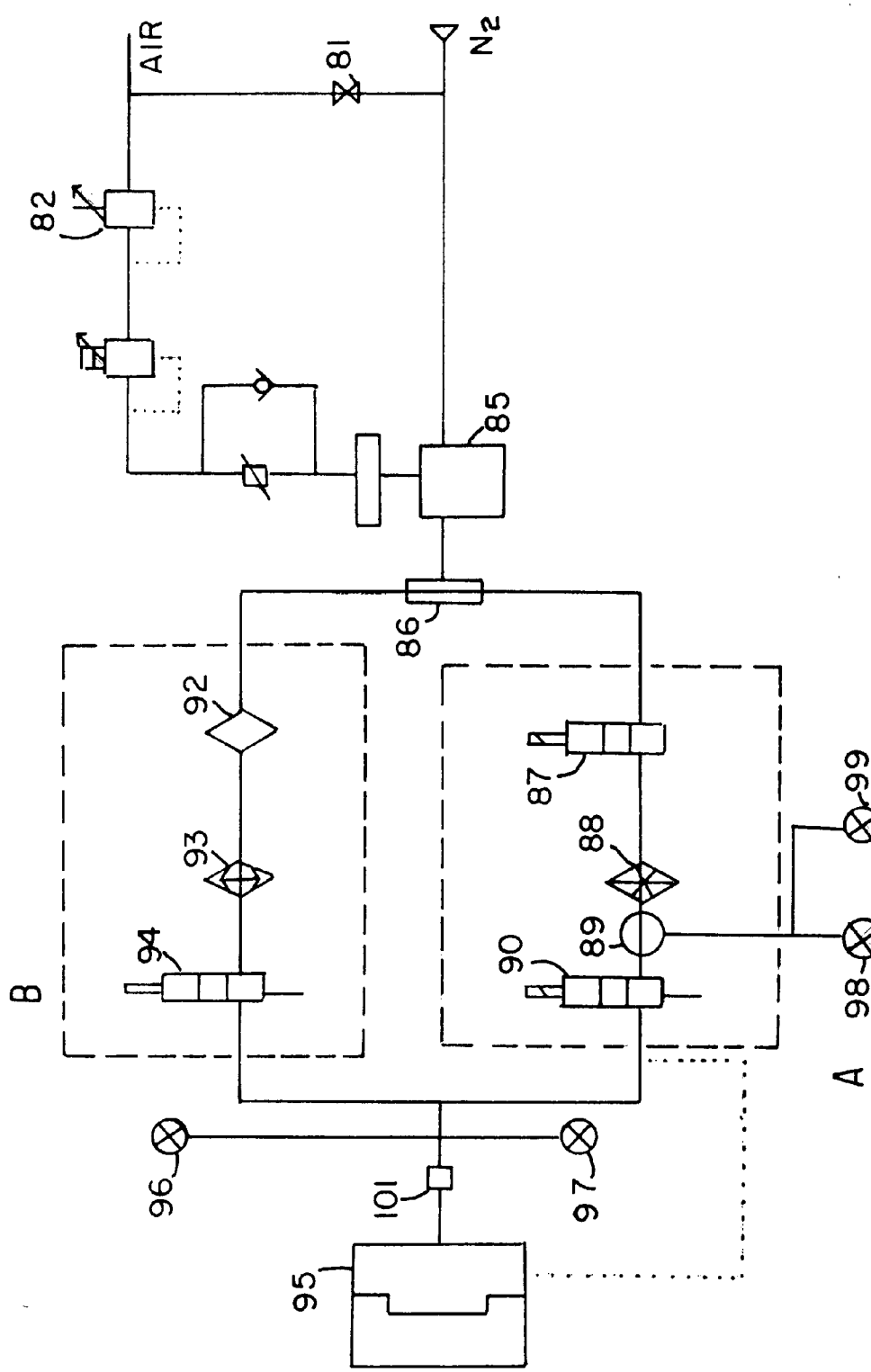
FIG. 12 is a schematic representation of the components for heating and cooling gas utilized with the present invention.

The system 76, as shown in FIG. 12, may be arranged to operate and allow for pressurization of $N_2$ by the gas ($N_2$) itself or shop air (150 psi), whichever suits the need.

If $N_2$ is not used as a control mechanism, the Tee fitting 81 and gas regulator 82 would be eliminated from the overall system operation. The high pressure gas (up to 15,000 psi) would be used as both the control mechanism as well as the actual set pressure gas to hollow out the molten plastic. A proportional regulator would provide precise pressure control with a flow control valve loading a "Dome" loaded high pressure regulator 85 to make the gas setpoint (set on the PID controller). Another Tee fitting 86 would be used as a split for the gas injection stage, shown as the first circuit "A", in FIG. 12, and the gas packing/holding/cooling state, shown as the second circuit "B" in FIG. 12.

During the gas injection stage, once the gas has reached the setpoint at the "dome" regulator 85, circuit A would allow the actuation of a 2 way solenoid valve 87. At this point, a heat exchanger heating element 88 would heat the gas to a desired set temperature and fill the gas into the accumulator 89. At this point, both the pressure and the temperature would be measured by a pressure transducer 98 and a temperature sensor 99. Next, a solenoid valve 90 would open and allow the free passage of pressurized gas through a fixed jewel orifice 101 and into the mold cavity 95. A pressure sensor 96 and a temperature sensor 97 would be placed before the jeweled orifice 101 to measure the pressure and temperature just before the gas enter the mold 95.

Upon the completion of gas injection cycle, the solenoid valves 90 and 87 would close. The $N_2$ would now be diverted to circuit B where a humidifier device 92 would add small amounts of $H_2O$ to the $N_2$ and the components would be cooled to a set temperature by a heat exchanger cooling element 93. Again, a 2 way solenoid valve would open 94 allowing the mixture to pass through the orifice 101 with pressure sensor 96 and temperature sensor 97 recording the pressure and temperature of the cold mixture. This phase of the cycle would assist in making hollow parts.

Thus the present invention includes a gas injection molding system comprising a screw for delivering plastic material to a mold. It also includes a gas injection jeweled orifice port through the screw tip for injecting gas, vapor, or liquids into the plastic being molded.

The gas injection may use a menu driven system allowing various time/pressure durations in the gas injection phase and the gas holding/packing phase. This can be either a personal computer (PC), Programmable Logic controller (PLC) or an embedded system with either a Proportional Integral Derivative (PID) or FUZZY logic algorithm. The temperature of the gas may be controlled during the injection phase and cooling phase via the control system.

I claim:

1. A method for injection molding in which a gas, vapor or liquid is delivered into a melted plastic downstream of an elongated screw shaft having a longitudinal axis, which screw shaft is rotatably and reciprocably supported within a housing of an injection molding machine, said screw shaft having a proximal end and a distal tip end, said delivery arranged to effect changes within that plastic, said method comprising the steps of:

providing a bore through said screw shaft from said proximal end to said distal tip end and out through said distal tip end;

rotating said screw shaft in said housing to drive said plastic along a path between said screw shaft and said housing, and downstream of said screw shaft;

moving said reciprocably movable screw shaft along its longitudinal axis in said injection molding machine; and introducing said gas, vapor or liquid into said bore to permit said gas, liquid or vapor to be delivered through said bore of said screw shaft and out said distal tip end thereof, and into said melted plastic for injection into a mold by said reciprocably movable screw shaft downstream of said screw shaft.

2. The method of injection molding in which a gas, vapor or liquid is delivered into a melted plastic downstream of an elongated screw shaft in said injection molding machine, as recited in claim 1, including the step of:

attaching a coupling to said reciprocably movable screw shaft in communication with said bore, to permit said gas, vapor or liquid to be delivered through said bore, and into said melted plastic at said distal tip end of said screw shaft.

3. The method of injection molding in which a gas, vapor or liquid is delivered into a melted plastic downstream of an elongated screw shaft in said injection molding machine, as recited in claim 2, including the step of:

arranging at least one conduit spaced within said bore of said reciprocably movable screw shaft, so as to permit separate transfer of multiple gases, liquids or vapors simultaneously into said plastic melt at said distal end of said screw shaft.

4. The method of injection molding in which a gas, vapor or liquid is delivered into a melted plastic downstream of an elongated screw shaft in said injection molding machine, as recited in claim 1, including the step of:

introducing said gas, liquid or vapor sequentially through said bore and into said melted plastic downstream of said reciprocably movable screw shaft, so as to introduce a bubble of said gas, liquid or vapor into said melted plastic at said downstream end of said screw shaft.

5. The method of injection molding in which a gas, vapor or liquid is delivered into a melted plastic downstream of an elongated screw shaft of an injection molding machine, as recited in claim 2, including the step of:

providing a radially directed opening from said bore to said coupling to provide fluid communcation from said coupling to said distal tip end of said screw shaft.

6. A method for the delivery of at least one fluid into a melted plastic in a mold downstream of an elongated screw shaft in an injection molding machine, which screw shaft is rotatably and reciprocably movably supported within a housing, said screw shaft having a proximal end and a distal tip end, said delivery of said fluid arranged to effect changes to that plastic, said method comprising the steps of:

providing a bore through said screw shaft from said proximal end to said distal tip end and out through said distal tip end thereof;

rotating said screw shaft in said housing to drive plastic about said screwshaft and into said housing downstream of said screw shaft;

reciprocably moving said screw shaft in said housing in said injection molding machine to inject plastic into said mold; and introducing said fluid into said bore to permit said fluid to be delivered through said bore and out said distal tip end of said reciprocably movable screw shaft and into said molten plastic at the downstream end of said screw shaft; and injecting said fluid into said mold.

7. The method for the delivery of at least one fluid into a melted plastic downstream of an elongated, reciprocably movable screw shaft of an injection molding machine, as recited in claim 6, wherein said fluid is selected from the group consisting of: a gas, a liquid or a vapor.

8. The method for the delivery of at least one fluid into a melted plastic downstream of an elongated screw shaft of an injection molding machine as recited in claim 6, including the step of:

introducing said fluid into said bore through a coupling attached to said reciprocably movable screw shaft.

9. The method for the delivery of at least one fluid into a melted plastic downstream of an elongated screw shaft of an injection molding machine as recited in claim 8, including the step of:

attaching said coupling to said reciprocably movable screw shaft at said proximal end of said screw shaft.

\* \* \* \* \*